(12) United States Patent
Miyazaki et al.

(10) Patent No.: US 9,341,633 B2
(45) Date of Patent: May 17, 2016

(54) METHOD FOR PRE-TREATING SAMPLE CONTAINING GLYCATED HEMOGLOBIN

(75) Inventors: Osamu Miyazaki, Ryugasaki (JP); Syunsuke Kurashita, Ryugasaki (JP); Kohei Takubo, Ryugasaki (JP)

(73) Assignee: SEKISUI MEDICAL CO., LTD., Tokyo (JP)

( * ) Notice: Subject to any disclaimer, the term of this patent is extended or adjusted under 35 U.S.C. 154(b) by 160 days.

(21) Appl. No.: 13/139,239

(22) PCT Filed: Dec. 10, 2009

(86) PCT No.: PCT/JP2009/006769
§ 371 (c)(1),
(2), (4) Date: Jun. 10, 2011

(87) PCT Pub. No.: WO2010/067612
PCT Pub. Date: Jun. 17, 2010

(65) Prior Publication Data
US 2011/0318765 A1    Dec. 29, 2011

(30) Foreign Application Priority Data
Dec. 11, 2008    (JP) .................................. 2008-316174

(51) Int. Cl.
*G01N 33/72*    (2006.01)
(52) U.S. Cl.
CPC .......... *G01N 33/723* (2013.01); *G01N 2400/02* (2013.01); *G01N 2440/38* (2013.01)
(58) Field of Classification Search
CPC ............ G01N 33/723; G01N 2400/02; G01N 2440/38
USPC .............. 435/7.25, 7.92, 7.93, 7.94, 7.95, 14, 435/961, 962, 973; 436/518, 534, 8, 17, 18, 436/66, 67, 174, 175, 176, 177, 825, 826; 530/387.9, 388.7, 389.6
See application file for complete search history.

(56) References Cited

U.S. PATENT DOCUMENTS

| | | | |
|---|---|---|---|
| 3,799,264 A | | 3/1974 | Cardenas et al. |
| 4,647,654 A | | 3/1987 | Knowles et al. |
| 4,658,022 A | * | 4/1987 | Knowles et al. ............... 530/402 |
| 4,970,171 A | | 11/1990 | Messenger et al. |
| 5,470,759 A | * | 11/1995 | Sugiyama et al. ............ 436/541 |
| 5,541,117 A | | 7/1996 | Karl et al. |
| 6,294,062 B1 | * | 9/2001 | Buck et al. ..................... 204/400 |
| 2002/0173043 A1 | * | 11/2002 | Merabet et al. ................. 436/66 |
| 2003/0180967 A1 | | 9/2003 | Shigetoh |
| 2005/0101771 A1 | | 5/2005 | Kouzuma et al. |
| 2008/0293074 A1 | | 11/2008 | Tanaka et al. |

FOREIGN PATENT DOCUMENTS

| | | |
|---|---|---|
| CN | 101160527 | 4/2008 |
| EP | 0 185 870 A2 | 7/1986 |
| EP | 0 185 870 A3 | 7/1986 |
| EP | 0 407 860 A2 | 1/1991 |
| JP | 07-51087 | 2/1995 |
| JP | 7 23891 | 3/1995 |
| JP | 2001 33442 | 2/2001 |
| JP | 2002 340899 | 11/2002 |
| JP | 2003 344397 | 12/2003 |
| JP | 3512545 | 1/2004 |
| JP | 2007 163182 | 6/2007 |
| WO | 02 21142 | 3/2002 |
| WO | 02 61119 | 8/2002 |
| WO | WO 02/088185 A2 | 11/2002 |
| WO | WO 02/088185 A3 | 11/2002 |
| WO | WO02/090539 A2 | 11/2002 |

OTHER PUBLICATIONS

International Search Report issued Jan. 26, 2010 in PCT/JP09/06769 filed Dec. 10, 2009.
U.S. Appl. No. 13/139,201, filed Jun. 10, 2011, Miyazaki, et al.
Extended European Search Report issued Jul. 6, 2012 in Patent Application No. 09831718.3.
Office Action issued in European Patent Application No. 09831718.3 issued Jun. 9, 2013, 5 pp.
Chinese Office Action issued Jun. 3, 2013 in corresponding Chinese Application No. 200980149846.9, 7pp., p. 6 only.
Zhang Chang-li, "Determine Glycosylated Hemoglobin Using Immune Agglutination Method", Journal of Anhui Health Vocational & Technical College, vol. 7, No. 5, Oct. 31, 2008, pp. 83-84 (with English abstract in the p. 84).

* cited by examiner

*Primary Examiner* — Gail R Gabel
*Assistant Examiner* — James L Grun
(74) *Attorney, Agent, or Firm* — Oblon, McClelland, Maier & Neustadt, L.L.P.

(57) ABSTRACT

There are provided a pre-treatment technique for a glycated hemoglobin-containing sample, which is a simple and convenient treatment, is free from problems in storage stability and environmental aspects, and is capable of exposing an epitope sufficiently in a short time; and an method for an immunological assay of glycated hemoglobin using this technique.
A method for pre-treating a glycated hemoglobin-containing sample for an immunological assay of glycated hemoglobin, the method includes treating a glycated hemoglobin-containing sample with a pre-treatment solution containing (A) guanidine or a salt thereof and (B) a nonionic surfactant and/or a nitrite.

13 Claims, 5 Drawing Sheets

SEQUENCE LISTING

```
<160> NUMBER OF SEQ ID NOS: 3

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence: Designed
      peptide based on glycohemoglobin

<400> SEQUENCE: 1

Val His Leu Thr Pro Glu
1               5

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: Designed
      peptide based on glycohemoglobin

<400> SEQUENCE: 2

Val His Leu Thr Cys
1               5

<210> SEQ ID NO 3
<211> LENGTH: 11
<212> TYPE: PRT
<213> ORGANISM: Artificial Sequence
<220> FEATURE:
<223> OTHER INFORMATION: Description of Artificial Sequence: Designed
      peptide based on glycohemoglobin

<400> SEQUENCE: 3

Val His Leu Thr Pro Glu Glu Lys Tyr Tyr Cys
1               5                   10
```

METHOD FOR PRE-TREATING SAMPLE CONTAINING GLYCATED HEMOGLOBIN

CROSS-REFERENCE TO RELATED APPLICATIONS

The present application is a 35 U.S.C. §371 National Stage patent application of International patent application PCT/JP2009/006769, filed on Dec. 10, 2009, which claims priority to Japanese patent application JP 2008-316174, filed on Dec. 11, 2008.

FIELD OF THE INVENTION

The present invention relates to a method for accurately measuring glycated hemoglobin, particularly glycated hemoglobin A1c, by an immunological technique.

BACKGROUND OF THE INVENTION

Glycated hemoglobin (glycohemoglobin) in which sugar is bonded to hemoglobin in blood, particularly hemoglobin A1c (hereinafter, referred to as "HbA1c") in which the N-terminal valine residue of the β-chain of hemoglobin is glycated, clinically reflects the average blood sugar level of the past one to two months. Therefore, glycated hemoglobin, or glycated hemoglobin A1c, is widely used as a marker appropriate for the diagnosis of diabetes or a clinical observation of diabetes.

As the method for measuring glycated hemoglobin, HPLC methods and immunological assay methods are known, but in the immunological assay methods, it is required to use antibodies that are specific to the glycated site of hemoglobin. It has been found that the glycation site at the N-terminal of the β-chain of hemoglobin is not present on the surface of the protein but is embedded inside of the protein, and the glycation site is present at a place where it is difficult for an antibody to bind to the glycation site. Therefore, in order to allow an antibody that recognizes the relevant epitope site to react efficiently, a technology for exposing the relevant epitope site to the surface is being developed (Patent Document 1).

As the technique for epitope exposure, there are known techniques for treating a glycated hemoglobin-containing sample by using each of guanidine, thiocyanic acid, or lithium thiocyanate alone, by combining thiocyanic acid with an oxidizing agent such as ferricyanide, and by an ionic surfactant, a nonionic surfactant or the like (Patent Documents 1 to 6).

PRIOR ART

Patent Documents

Patent Document 1: Japanese Patent Application Laid-Open No. 61-172064
Patent Document 2: Japanese Patent Application Laid-Open No. 01-155268
Patent Document 3: Japanese Patent Application Laid-Open No. 03-51759
Patent Document 4: Japanese Patent Application Laid-Open No. 06-11510
Patent Document 5: Japanese Patent Application Laid-Open No. 2001-33442
Patent Document 6: Japanese Patent Application Laid-Open

SUMMARY OF THE INVENTION

However, in connection with the conventional techniques for epitope exposure, for example, a guanidine treatment requires a heating treatment. Thiocyanic acid is an environmentally harmful substance. An oxidizing agent such as ferricyanide has a problem with storage stability, such as being susceptible to coloration. A nonionic surfactant, when used alone, has a problem that the effects are not sufficiently exhibited.

It is therefore an object of the present invention to provide a pre-treatment technique for a glycated hemoglobin-containing sample, which is a simple and convenient treatment, is free from problems in storage stability and environmental aspects, and is capable of exposing an epitope sufficiently in a short time; and an immunological assay method for glycated hemoglobin using this technique.

The inventors of the present invention conducted an investigation on an efficient and convenient technique for epitope exposure in glycated hemoglobin, and the inventors found that when a glycated hemoglobin-containing sample is treated with a solution containing guanidine, a nonionic surfactant and/or a nitrite, an extremely excellent effect of epitope exposure is obtained as compared with the case of using each of guanidine, a nonionic surfactant and a nitrite alone, and that the glycated part is exposed highly efficiently in a short time even though the sample is not subjected to a heating treatment, so that an accurate immunological assay of glycated hemoglobin is made possible. Thus, the inventors completed the present invention.

That is, the present invention is to provide a method for pre-treating a glycated hemoglobin-containing sample for an immunological assay of glycated hemoglobin, which includes treating a glycated hemoglobin-containing sample with a pre-treatment solution containing (A) guanidine or a salt thereof and (B) a nonionic surfactant and/or a nitrite.

Further, the present invention is to provide a pre-treatment solution for a glycated hemoglobin-containing sample intended for an immunological assay of glycated hemoglobin, which contains (A) guanidine or a salt thereof and (B) a nonionic surfactant and/or a nitrite.

Furthermore, the present invention is to provide a method for an immunological assay of glycated hemoglobin in a glycated hemoglobin-containing sample, which includes treating a glycated hemoglobin-containing sample with a pre-treatment solution containing (A) guanidine or a salt thereof and (B) a nonionic surfactant and/or a nitrite, and then performing an immunological assay using an anti-glycated hemoglobin antibody.

According to the pre-treatment method of the present invention, the glycated part of glycated hemoglobin in a sample is efficiently exposed by a simple and convenient treatment in a short time. Therefore, when an immunological assay using an anti-glycated hemoglobin antibody is carried out using a sample which has been subjected to the pre-treatment, an accurate quantitative assay of glycated hemoglobin can be achieved.

DESCRIPTION OF PREFERRED EMBODIMENTS

Figure 1:
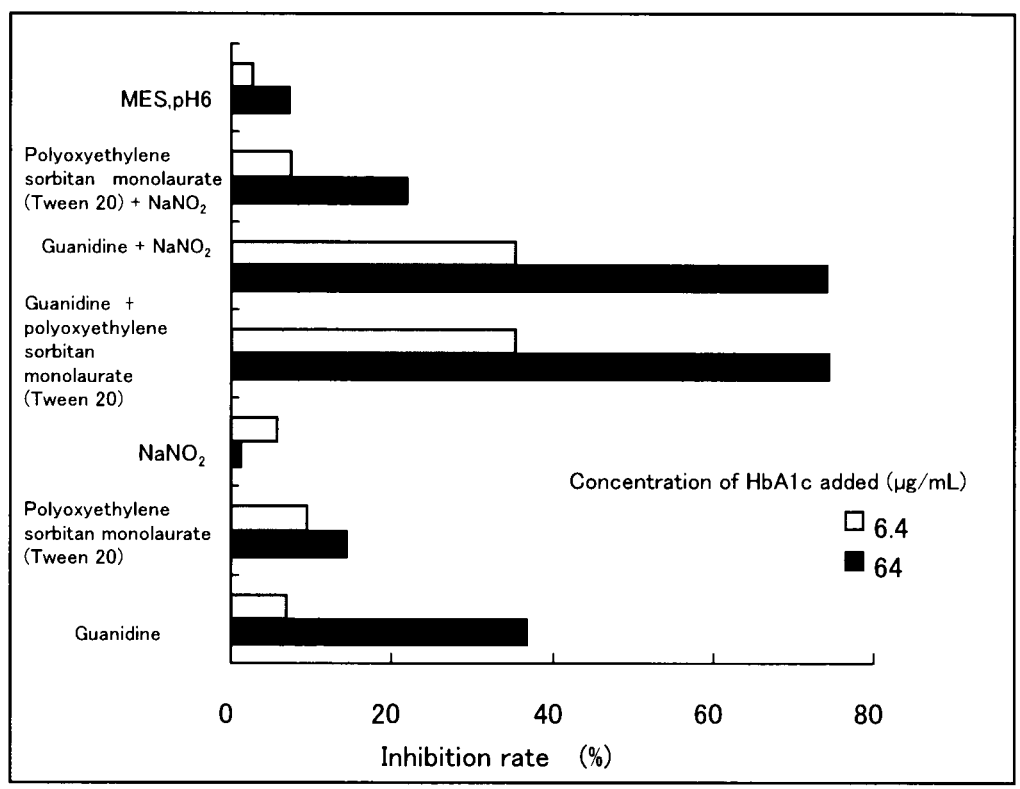
FIG. 1 shows the results of a comparison of the epitope exposure effects of various reagents, obtained by a competitive ELISA method.

The glycated hemoglobin-containing sample of the present invention is a test sample for measuring glycated hemoglobin, and examples of the sample include blood, a redblood cell fraction, and the like. Here, the glycated hemoglobin is preferably a glycated hemoglobin in which the β-chain of hemoglobin is glycated, and particularly, HbA1c is preferred.

Furthermore, the epitope part that is exposed by the method of the present invention is a glycated region of hemoglobin, and the epitope part is, for example, a glycated N-terminal region of the β-chain of hemoglobin, and more preferably a region containing a peptide in which the N-terminal valine of the β-chain of hemoglobin is glycated.

The pre-treatment solution that is used in the pre-treatment of the present invention contains (A) guanidine or a salt thereof and (B) a nonionic surfactant and/or a nitrite. According to the present invention, when the component (A) and the component (B) are used together, an extremely excellent effect of epitope exposure is obtained as compared with the case of using each of the component (A) and the component (B) alone.

In regard to the guanidine of the component (A), guanidine itself can be used, but it is particularly preferable to use a guanidine salt from the viewpoint of the effect of epitope exposure. A preferred example of the salt of guanidine is guanidine hydrochloride. The concentration for use of guanidine is preferably 1 mol/L to 6 mol/L, and particularly preferably 2.5 mol/L to 3.5 mol/L, from the viewpoints of the effect of epitope exposure and the reactivity of antibodies.

In regard to the nonionic surfactant of the component (B), examples include a polyoxyethylene alkyl ether, a polyoxyethylene alkyl phenyl ether, a polyoxyethylene polyoxypropylene ether, a polyoxyethylene fatty acid ester, a sucrose fatty acid ester, a polyoxyethylene sorbitan fatty acid ester, an alkyl glycoside, an alkanoyl-N-methylglucamide, an (alkylcarbamoyl) methyl-glucopyranoside, an alkyl glucopyranoside, a deoxycholic acidamide, saponin, and the like. More specific examples of the nonionic surfactant include a polyoxyethylene $C_6$-$C_{24}$ alkyl ether, a polyoxyethylene $C_6$-$C_{24}$ alkyl phenyl ether, a polyoxyethylene polyoxypropylene ether, a polyoxyethylene $C_6$-$C_{24}$ fatty acid ester, a sucrose $C_6$-$C_{24}$ fatty acid ester, a polyoxyethylene sorbitan $C_6$-$C_{24}$ fatty acid ester, a $C_6$-$C_{24}$ alkyl glycoside, a $C_6$-$C_{24}$ alkanoyl methylglucamide, a ($C_6$-$C_{24}$ alkylcarbamoyl) methyl-glucopyranoside, a $C_6$-$C_{24}$ alkyl glucopyranoside, N,N-bis(3-D-gluconamidopropyl)deoxycholamide, and saponin and the like.

The concentration for use of the nonionic surfactant is preferably 0.1 to 5%, and particularly preferably 0.2 to 1.50%, from the viewpoints of the effect of epitope exposure and the reactivity of antibodies.

In regard to the nitrite of the component (B), examples include alkali metal salts of nitrous acid, such as sodium nitrite and potassium nitrite.

The concentration for use of the nitrite is preferably 1 mmol/L to 50 mmol/L, and particularly preferably 5 mmol/L to 15 mmol/L, from the viewpoints of the effect of epitope exposure and the reactivity of antibodies.

The nonionic surfactant and the nitrite may be used separately or may be used together, but from the viewpoints of shortening the treatment time and enhancing the suitability to quantitative measurement, it is more preferable to use the nonionic surfactant and the nitrite together.

Furthermore, there are no particular limitations on the content ratio (mass ratio) of the component (A) and the component (B) in the pre-treatment solution of the present invention from the viewpoints of the effect of epitope exposure and the reactivity of antibodies, and the concentration ranges for the respective components described above may be in the ranges of 1 to 6 mol/L for the component (A), 0.1 to 5% for the nonionic surfactant of the component (B), and 1 to 50 mmol/L for the nitrite of the component (B), respectively.

It is preferable that the pre-treatment solution of the present invention be used as an aqueous solution containing the components (A) and (B). Furthermore, the pH value of this aqueous solution is preferably 4.0 to 9.0, and more preferably 4.5 to 7.0. An appropriate buffering agent may be added to the aqueous solution in order to adjust the pH to these values. Examples of the buffering agent that may be used include citric acid, phthalic acid, acetic acid, succinic acid, cacodylic acid, maleic acid, imidazole, collidine, phosphoric acid, universal buffer of Johnson-Lindsay and the like, Good's buffer such as 2-morpholinoethanesulfonic acid (hereinafter, referred to as "MES"), bis(2-hydroxyethyl)imino-tris(hydroxymethyl)methane (hereinafter, referred to as "Bis-Tris"), and piperazine-N,N'-bis(2-ethanesulfonic acid) (hereinafter, referred to as "PIPES") and the like.

In order to treat a glycated hemoglobin-containing sample using the pre-treatment solution of the present invention, the pre-treatment solution may be added to a glycated hemoglobin-containing sample solution, and the mixture may be stirred. The temperature is preferably 15° C. to 50° C., and more preferably 20° C. to 40° C. The treatment time is preferably 30 seconds to 30 minutes, and more preferably 1 minute to 5 minutes.

When the glycated hemoglobin in a glycated hemoglobin-containing sample is subjected to the treatment described above, the glycation site is efficiently exposed. Accordingly, when this treated sample is subjected to an immunological assay using an anti-glycated hemoglobin antibody, the content of glycated hemoglobin in the glycated hemoglobin-containing sample can be accurately measured.

As the method for measuring glycated hemoglobin in the method of the present invention, any conventional immunoassay method may be employed. Here, examples of the immunoassay method include a sandwich ELISA method, a competitive ELISA method, an immunochromatographic method, a latex agglutination method, a competitive latex agglutination method, and the like. Hereinafter, an explanation will be given by taking the measurement of HbA1c as an example.

For example, in the case of performing an assay by a sandwich ELISA method, HbA1c can be measured by a method such as described below, using purified HbA1c as a standard substance. That is, a specimen sample which has been treated with the pre-treatment solution of the present invention is added to an ELISA plate on which an anti-HbA1c antibody is immobilized, to allow the sample to react. Subsequently, an enzyme-labeled anti-hemoglobin antibody (hereinafter, referred to as "anti-Hb antibody") is allowed to react with the sample, and from the changes in the absorbance after color development, HbA1c that is present in the sample can be specifically measured.

In the case of performing an assay by a latex agglutination method, a measurement can be carried out by a method such as described below, using purified HbA1c as a standard substance. That is, when an anti-HbA1c antibody is bound to latex particles which serve as an insoluble carrier, and the latex particles are brought into contact with a specimen sample that has been treated with the pre-treatment solution of the present invention, and with an anti-Hb monoclonal antibody, the antibody-bound latex particles are crosslinked via the HbA1c in the sample, and undergo agglutination. Accordingly, from the changes in this degree of agglutination, the relevant HbA1c can be specifically measured.

In the case of performing an assay by a competitive latex agglutination method, a measurement can be carried out by a method such as described below, using purified HbA1c as a standard substance. That is, when the glycated N-terminal peptide of the β-chain of HbA1c, for example, glycated hexapeptide (f-VHLTPE (SEQ ID NO:1)), is bound to latex particles which serve as an insoluble carrier, and the latex particles are brought into contact with a specimen sample that has been treated with the pre-treatment solution of the present invention, and with an anti-HbA1c antibody, the HbA1c in the specimen sample exhibits competitive inhibition in the agglutination reaction between the f-VHLTPE-bound (SEQ ID NO: 1) latex particles and the anti-HbA1c antibody. Therefore, from the changes in this competitive inhibition, HbA1c in the specimen sample can be specifically measured.

There are no particular limitations on the latex particles of the antibody-bound latex particles that are used in the latex agglutination method or the like, as long as the particles serve as a carrier in the form of microparticles that is generally used in the immunological agglutination reactions and agglutination inhibition reactions utilizing a latex agglutination reaction. However, organic microparticles that can be industrially mass-produced are preferred. Examples of such organic microparticles include microparticles of a homopolymer or a copolymer of a vinyl-based monomer such as styrene, vinyl chloride, acrylonitrile, vinyl acetate, an acrylic acid ester, or a methacrylic acid ester; and a butadiene-based copolymer such as a styrene-butadiene copolymer or a methyl methacrylate-butadiene copolymer. Furthermore, reactive organic microparticles in which functional groups such as a carboxyl group, a primary amino group, a carbamoyl group, a hydroxyl group and an aldehyde group are bound to such organic microparticles, can also be used with preference. Among the latex particles described above, polystyrene-based latex particles of polystyrene, a styrene-butadiene copolymer or the like are preferred, from the viewpoint that the adsorbability of an antigen or an antibody to the latex particles is excellent, and the latex particles can stably maintain the biological activity for a long time.

There are no particular limitations on the shape of the latex particles, but the average particle size is preferably a size sufficient for visually or optically detecting the agglutination product produced as a result of an agglutination reaction between the protein on the surface of the latex particles and the substance as an object of measurement. The average particle size is preferably 0.02 to 1.6 μm, and particularly preferably 0.03 to 0.5 μm.

There are no particular limitations on the method of binding anti-HbA1c antibodies to latex particles, and any known method can be used. Examples include a method of physically adsorbing the antibody to the surface of latex particles, a method of covalently bonding the antibody to the surface of latex particles having a functional group, a method of performing sensitization by immunological binding, and the like.

Figure 5:
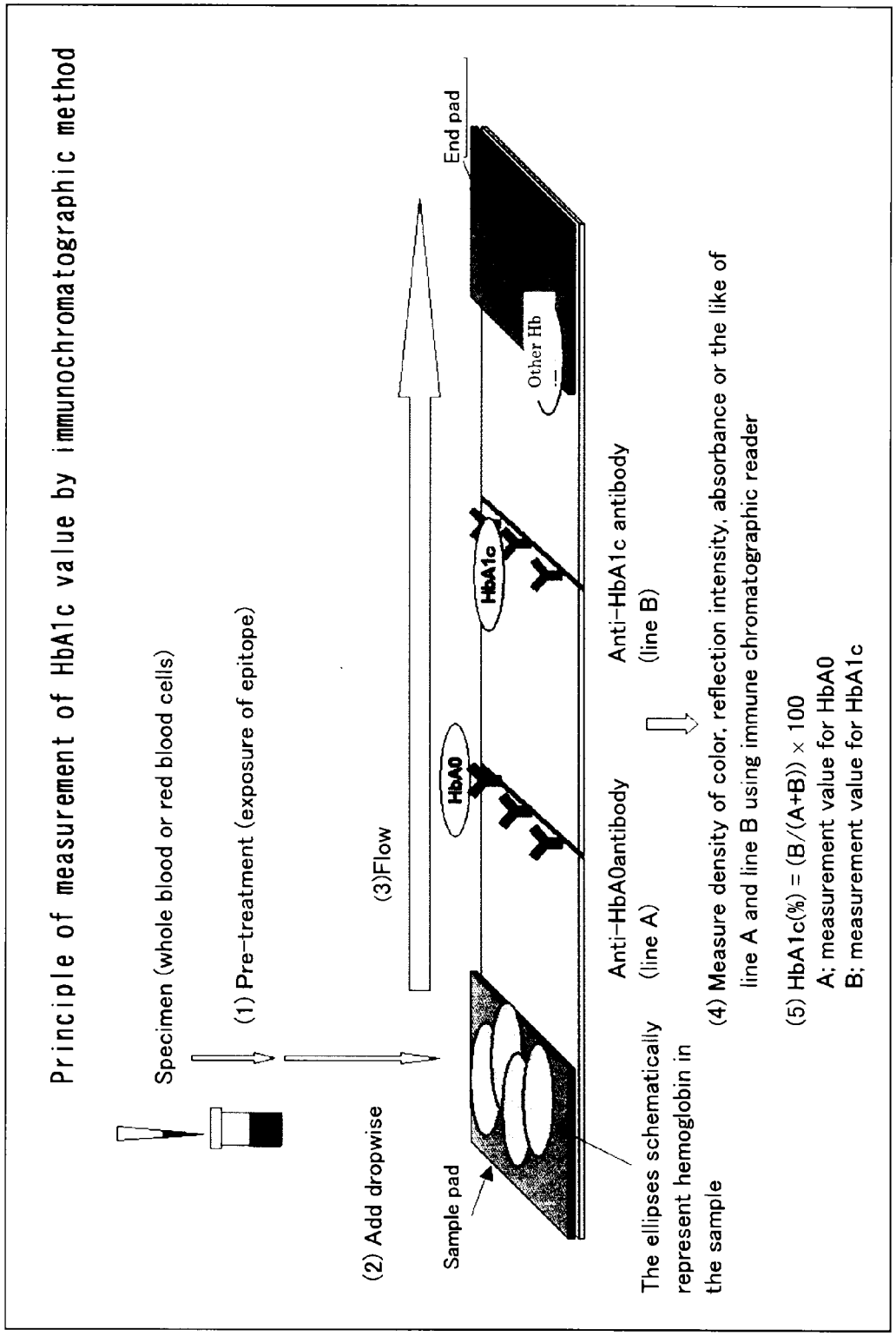
FIG. 5 is a schematic diagram showing a method for measuring HbA1c according to an immunochromatographic method.

In the case of performing an assay by an immunochromatographic method, hemoglobin A0 (hereinafter, referred to as "HbA0") in which the N-terminus of the β-chain of hemoglobin is not modified, and HbA1c can be simultaneously measured, and therefore, the method is particularly suitable. For example, as shown in FIG. 5, an immunochromatographic support on which an anti-HbA0 antibody and an anti-HbA1c antibody are respectively immobilized at different sites (line A and line B) is used. A HbA1c-containing specimen which has been treated with the pre-treatment solution of the present invention is added dropwise on the sample pad. The sample thus added dropwise flows by the capillary phenomenon, and when the sample reaches the line A, only HbA0 in the sample reacts. When the sample reaches the line B, only HbA1c in the sample reacts. Hemoglobins other than them migrate to the end pad without reacting. When the density of color, reflection intensity, absorbance or the like of the line A and the line B is measured with an immunochromatographic reader, HbA0 and HbA1c in the sample can be respectively measured. Here, when the quantification value of HbA0 is designated as A, and the quantification value of HbA1c as B, HbA1c (%) may be determined by the formula: HbA1c (%)=(B/(A+B))×100.

Here, the anti-HbA1c antibody may be a monoclonal antibody or a polyclonal antibody, and for example, those described in patent documents (Japanese Patent Application Laid-Open No. 61-172064, and Japanese Patent Application Laid-Open No. 06-66796) can be used.

EXAMPLES

Next, the present invention will be described in more detail by way of Examples.

Example 1

Comparison of Effects of Epitope Exposure (I) Materials and Methods (1) Preparation of Purified HbA0 and Purified HbA1c A human red blood cell lysate was subjected to an ion exchange chromatography using Bio-Rex70 (Bio-Rad Laboratories, Inc.), which is described in a non-patent literature (Melisenda J. McDonald, et al., JBC, 253(7), 2327-2332, 1978), to obtain purified HbA0 and HbA1c, and these were used in the subsequent experiments.

(2) Preparation of Various Peptides and Glycated Peptides

Peptides having various sequences were synthesized by a Fmoc method using an automatic peptide synthesizer, and were purified. It was confirmed by HPLC that the purity of each of the peptides was 95% or higher. Furthermore, it was confirmed with a mass analyzer (MALDI-TOF) that the respective molecular weights of the peptides were identical with the theoretical values. Glycated peptides were synthesized and purified by a method described in a patent document (Japanese Patent Application Laid-Open No. 61-172064). That is, peptides having various sequences and glucose were allowed to react in anhydrous pyridine to synthesize glycated peptides, and the glycated peptides were purified by HPLC. It was confirmed with a mass analyzer (MALDI-TOF) that the respective molecular weights of the glycated peptides were identical with the theoretical values, that is, the molecular weights obtained by adding 162 to the respective molecular weights of the peptides.

(3) Preparation of Peptide-Bound Proteins and Glycated Peptide-Bound Proteins

Among the peptides or glycated peptides prepared in the above section (2), those synthesized to have cysteine (C) at the C-terminus (for example, VHLTC (SEQ ID NO:2), and f-VHLTC (SEQ ID NO: 2)) were bound to carrier proteins in the following manner. That is, the peptide (VHLTC) (SEQ ID NO: 2) or the glycated peptide (f-VHLTC) (SEQ ID NO: 2) which had been dissolved in a 20 mmol/L phosphate buffer solution pH 7.2 (hereinafter, referred to as "PBS") containing 0.15 mol/L NaCl, to a concentration of 5 mg/mL, was mixed at a ratio of 1:1 with a maleimide-activated ovalbumin (OVA) (manufactured by Pierce Biotechnology, Inc.) dissolved in purified water at a concentration of 5 mg/mL. Subsequently, the mixtures were incubated for 2 hours at room temperature while moderately rotated, and were dialyzed in PBS before use (VHLTC-OVA (SEQ ID NO: 2), and f-VHLTC-OVA (SEQ ID NO: 2)).

(4) Preparation of Anti-Hemoglobin Antibody, Anti-HbA1c Antibody, and Anti-HbA0 Antibody For the anti-hemoglobin antibody, a mouse monoclonal antibody produced by a routine method using the purified HbA0 obtained in the above section (1) as an immunogen, was used. For the anti-HbA1c antibody, a mouse monoclonal antibody produced by a method described in a patent document (Japanese Patent Application Laid-Open No. 61-172064) was used. That is, a glycated peptide (f-VHLT-PEEKYYC) (SEQ ID NO:3) synthesized in the above section (2) was bound to keyhole limpet hemocyanin (hereinafter, referred to as KLH), and this product was used as an immunogen. In the screening of a hybridoma, a strain which reacts with purified HbA1c but does not react with purified HbA0 in antigen-immobilized ELISA, was selected. For the anti-HbA0 antibody, a mouse monoclonal antibody produced by a routine method using, as an immunogen, the peptide-bound protein (VHLTC-OVA) (SEQ ID NO: 2) prepared in the above section (3), was used. At this time, in the screening of a hybridoma, a strain which reacts with purified HbA0 but does not react with purified HbA1c in antigen-immobilized ELISA, was selected.

In regard to the anti-HbA0 antibody, the strain selected by the screening was subjected to cloning, and a hybridoma which produces an anti-HbA0 monoclonal antibody was deposited with the International Patent Organism Depositary, National Institute of Advanced Industrial Science and Technology (dated Nov. 28, 2008; Tsukuba Central 6, 1-1-1 Higashi, Tsukuba, Ibaraki, Japan). The Accession Number is as follows.

Antibody No.: 85201
Accession No.: FERM BP-11187

(5) Specimen Treatment Method

Human red blood cells were mixed with each of various treatment solutions at a ratio of 1:50, and treated at 25° C. for 10 minutes. Then each of the mixtures was diluted 4-fold (HbA1c concentration: 64 µg/mL), 40-fold (HbA1c concentration: 6.4 µg/mL) and 400-fold (HbA1c concentration: 0.64 µg/mL) with 1% BSA-0.05% Tween 20-PBS (hereinafter, referred to as "1% BSA-PBST"), and were provided for the competitive ELISA which will be described below.

(6) Competitive ELISA a. The f-VHLTC-OVA (SEQ ID NO: 2) prepared in the above section (3) was diluted with PBS to a concentration of 1 µg/mL, and then the dilution was dispensed on a 96-well plate in an amount of 50 µL/well. The plate was left to stand overnight at 4° C.

b. The plate was washed three times with 400 µL/well of 0.05% Tween 20-PBS (hereinafter, referred to as "PBST"), and then a blocking solution (1% BSA-PBST) was dispensed on the plate in an amount of 100 µL/well. The plate was left to stand for one hour at room temperature.

c. The plate was washed three times with PBST, and then the specimen solution prepared in the above section (5) was dispensed on the plate in an amount of 25 µL/well.

d. Subsequently, the anti-HbA1c antibody diluted with 1% BSA-PBST to a concentration of 0.5 µg/mL was dispensed on the plate in an amount of 25 µL/well. The plate was left to stand for one hour at room temperature.

e. The plate was washed three times with PBST, and then a solution prepared by diluting HRP-GtF(ab')$_2$-Anti-Mouse Ig's (manufactured by Biosource, Inc.) to 5000-fold with 1% BSA-PBST, was dispensed on the plate in an amount of 50 µL/well. The plate was left to stand for one hour at room temperature.

f. The plate was washed three times with PBST, and then a color developing solution in which ortho-phenylenediamine hydrochloride (ortho-phenylenediamine hydrochloride (manufactured by Tokyo Chemical Industry Co., Ltd.) and hydrogen peroxide were dissolved in a citrate buffer solution at pH 5.0 to concentrations of 2 mg/mL and 0.02%, respectively) (hereinafter, referred to as "OPD color developing solution), was dispensed on the plate (50 µL/well). The plate was left to stand for 10 minutes at room temperature.

g. 0.75 mol/L sulfuric acid was dispensed on the plate in an amount of 50 µL/well to stop the reaction, and then the absorbance at 492 nm was measured with a plate reader.

(7) Calculation of Inhibition Rate

The inhibition rate was calculated by the following formula based on the absorbance values obtained in the above section (6), and the inhibition rate was used as an index for the effect of epitope exposure of the various reagents.

$$\text{Inhibition rate (\%)}=[(A-B)/A]\times 100$$

A: Absorbance in the absence of specimen
B: Absorbance in the presence of specimen (II) Results (1) Comparison of Exposure Effects of Various Reagents As pre-treatment solutions, respective aqueous solutions of 3 mol/L guanidine hydrochloride, 1% polyoxyethylene sorbitan monolaurate (Tween 20), and 1 mmol/L sodium nitrite; a 1:1-mixed solution of 6 mol/L guanidine hydrochloride and 2% polyoxyethylene sorbitan monolaurate (guanidine+polyoxyethylene sorbitan monolaurate); a 1:1-mixed solution of 6 mol/L guanidine hydrochloride and 20 mmol/L sodium nitrite (guanidine+NaNO$_2$); a 1:1-mixed solution of 2% polyoxyethylene sorbitan monolaurate and 20 mmol/L sodium nitrite (polyoxyethylene sorbitan monolaurate+NaNO$_2$); and a 5 mmol/L MES buffer solution (pH 6.0) were used to treat specimens in the same manner as in the above section (5) of (I). Subsequently, a comparison was made on the effects of exposure by competitive ELISA. As a result, as shown in FIG. 1, it was found that the combinations of guanidine+polyoxyethylene sorbitan monolaurate and guanidine+NaNO$_2$ exhibited markedly higher effects of exposure as compared with the pre-treatment solution of guanidine alone. On the other hand, the respective pre-treatment solutions using polyoxyethylene sorbitan monolaurate, sodium nitrite and MES buffer solution alone, and the combination of polyoxyethylene sorbitan monolaurate+NaNO$_2$, hardly exhibited any effect of exposure. These results suggest that the effect of epitope exposure is significantly increased by adding polyoxyethylene sorbitan monolaurate or sodium nitrite to a solution of guanidine hydrochloride.

(2) Type of Surfactant

As pre-treatment solutions, reagents prepared by adding various nonionic surfactants to a 3 mol/L solution of guanidine hydrochloride at a final concentration of 1%, 0.5% or 0.25%, were used to treat specimens. Subsequently, a comparison was made on the effects of epitope exposure of the various reagents by competitive ELISA. As a result, as shown in Table 1, it was found that the effects of epitope exposure were significantly higher in the reagents to which various surfactants were added than in the reagent of guanidine hydrochloride alone. These results suggest that the effect of epitope exposure is increased by adding a nonionic surfactant to a solution of guanidine hydrochloride.

TABLE 1

| Surfactant | Concentration (%) | Inhibition rate (%) |
|---|---|---|
| Guanidine | — | 40 |
| Polyoxyethylene(23) lauryl ether | 1 | 71 |
|  | 0.5 | 78 |
|  | 0.25 | 68 |
| Methyl-6-O-(N-heptylcarbamoyl)-α-D-glucopyranoside (HECAMEG) | 1 | 79 |
|  | 0.5 | 56 |
|  | 0.25 | 46 |
| n-octanoyl-N-methylglucamide (MEGA-8) | 1 | 53 |
|  | 0.5 | 53 |
|  | 0.25 | 53 |
| n-nonanoyl-N-methylglucamide (MEGA-9) | 1 | 78 |
|  | 0.5 | 67 |
|  | 0.25 | 56 |
| n-decanoyl-N-methylglucamide (MEGA-10) | 1 | 72 |
|  | 0.5 | 75 |
|  | 0.25 | 55 |
| n-octyl-β-D-glucopyranoside | 1 | 72 |
| Polyoxyethylene(80) polyoxypropylene(30) polyoxyethylene(80) (Pluronic F-68) | 1 | 66 |
|  | 0.5 | 46 |
| Polyoxyethylene sorbitan monolaurate (Tween 20) | 1 | 79 |
|  | 0.5 | 72 |
|  | 0.25 | 59 |
| Polyoxyethylene sorbitan monolaurate (Tween 80) | 1 | 72 |
|  | 0.5 | 65 |
|  | 0.25 | 58 |
| Polyoxyethylene nonyl phenyl ether(Nonidet P40) | 1 | 76 |
|  | 0.5 | 69 |
|  | 0.25 | 66 |
| Sucrose monolaurate | 1 | 71 |
|  | 0.5 | 74 |
|  | 0.25 | 70 |
| Polyoxyethylene octyl phenyl ether (Triton X-100) | 1 | 70 |
|  | 0.5 | 67 |
|  | 0.25 | 65 |
| Polyoxyethylene octyl phenyl ether (Triton X-114) | 1 | 70 |
|  | 0.5 | 65 |
|  | 0.25 | 60 |
| n-dodecyl-β-D-maltoside (DDM) | 1 | 64 |
|  | 0.5 | 71 |
|  | 0.25 | 67 |
| Octyl-β-D-thioglucopyranoside | 1 | 74 |
|  | 0.5 | 74 |
|  | 0.25 | 51 |
| Saponin | 1 | 60 |
|  | 0.5 | 48 |

(3) Effect of pH

Figure 2:
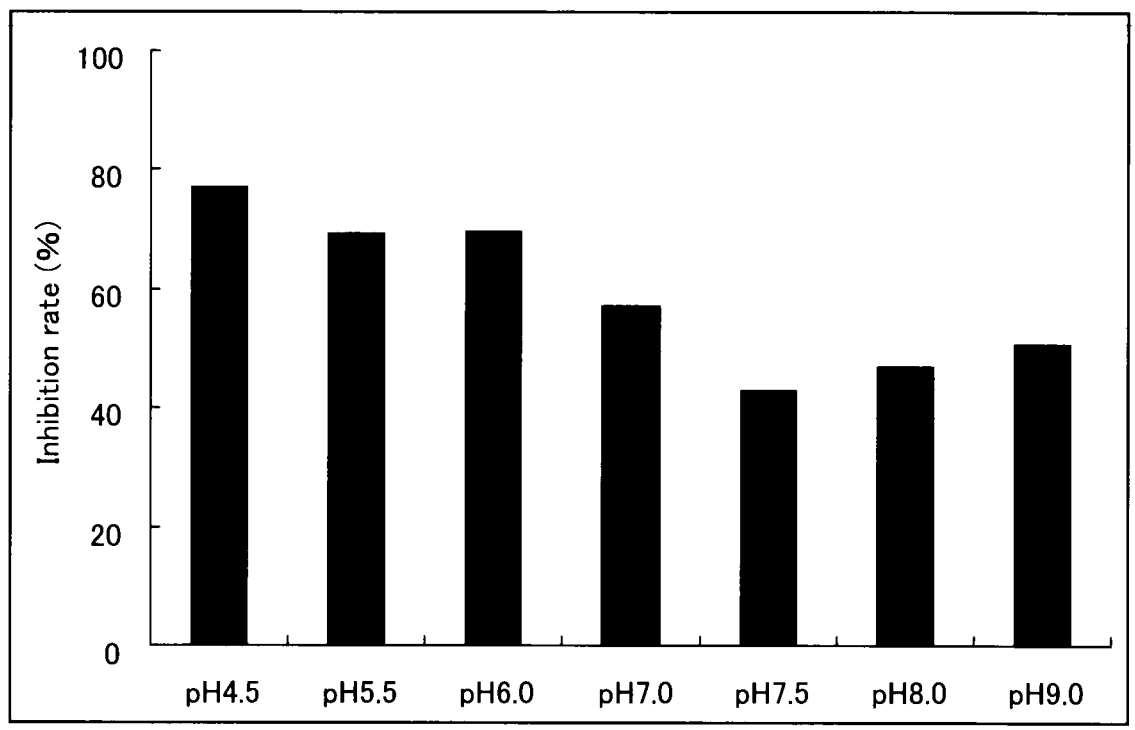
FIG. 2 shows the results of an examination of the influence of pH on the epitope exposure effects of the reagent of the present invention, obtained by a competitive ELISA method.

As pre-treatment solutions, buffer solutions at various pH values containing guanidine hydrochloride at a final concentration of 3 mol/L and polyoxyethylene sorbitan monolaurate (Tween 20) at a final concentration of 1% (pH 4.5 and pH 5.5: citric acid-$NaHPO_4$; pH 6.0 and pH 7.0: $KH_2PO_4$—$Na_2HPO_4$; pH 7.5, pH 8.0, and pH 9.0: Tris-HCl, respectively 20 mmol/L) were used to treat specimens. Subsequently, a comparison was made on the effects of epitope exposure of the various reagents by competitive ELISA. As a result, as shown in FIG. 2, it was found that the effect of epitope exposure was higher in the acidic region of pH 4.5 to pH 7, and particularly pH 4.5 to pH 6.

(4) Comparison at Treatment Time of One Minute

The specimen treatment time was changed from 10 minutes to 1 minute, and a comparison was made on the effects of epitope exposure of various reagents. As pre-treatment solutions, a buffer solution of 5 mmol/L MES (pH 6.0), and reagents prepared by adding the following various reagents, that is, 3 mol/L guanidine hydrochloride, 10 mmol/L sodium nitrite, 1% polyoxyethylene sorbitan monolaurate (Tween 20), 3 mol/L guanidine hydrochloride–1% polyoxyethylene sorbitan monolaurate (guanidine+polyoxyethylene sorbitan monolaurate), 3 mol/L guanidine hydrochloride–10 mmol/L sodium nitrite (guanidine+$NaNO_2$), 10 mmol/L sodium nitrite–1% polyoxyethylene sorbitan monolaurate (polyoxyethylene sorbitan monolaurate+$NaNO_2$), or 3 mol/L guanidine hydrochloride–10 mmol/L sodium nitrite–1% polyoxyethylene sorbitan monolaurate (guanidine+$NaNO_2$+polyoxyethylene sorbitan monolaurate), to the buffer solution were used. One volume of red blood cells was mixed with 50 volumes of each of the pre-treatment solutions, and then the mixtures were treated for one minute at 25° C. Thereafter, the specimens were diluted with 1% BSA-PBST in the same manner as in the above section (5) of (I), and a comparison was made on the effects of exposure by competitive ELISA. As a result, as shown in Table 2, it was found that the reagent prepared by adding guanidine+$NaNO_2$+polyoxyethylene sorbitan monolaurate exhibited the highest effect of exposure.

TABLE 2

| Treatment solution | Inhibition rate(%) |
|---|---|
| MES, pH 6.0 | 0.0 |
| Guanidine | 2.9 |
| $NaNO_2$ | 0.0 |
| Polyoxyethylene monolaurate (Tween 20) | 2.0 |
| Guanidine + polyoxyethylene monolaurate (Tween 20) | 30.5 |
| Guanidine + $NaNO_2$ | 28.7 |
| $NaNO_2$ + polyoxyethylene monolaurate (Tween 20) | 1.4 |
| Guanidine + $NaNO_2$ + polyoxyethylene monolaurate (Tween 20) | 37.9 |

Example 2

Stability of Reagents (I) Materials and Methods

In order to examine the storage stability of the pre-treatment solution of the present invention, a pre-treatment solution (1% polyoxyethylene sorbitan monolaurate (Tween 20)–mmol/L $NaNO_2$–3 mol/L guanidine hydrochloride–5 mmol/L MES buffer solution, pH 6.0) was left to stand for 8 days at 4° C. or at 37° C., and then the effect of epitope exposure was examined in the same manner as in Example 1. Thus, the effect of the pre-treatment solution was compared with the effect of epitope exposure of a reagent of the same formulation which was prepared on the test day.

(II) Results

Figure 3:
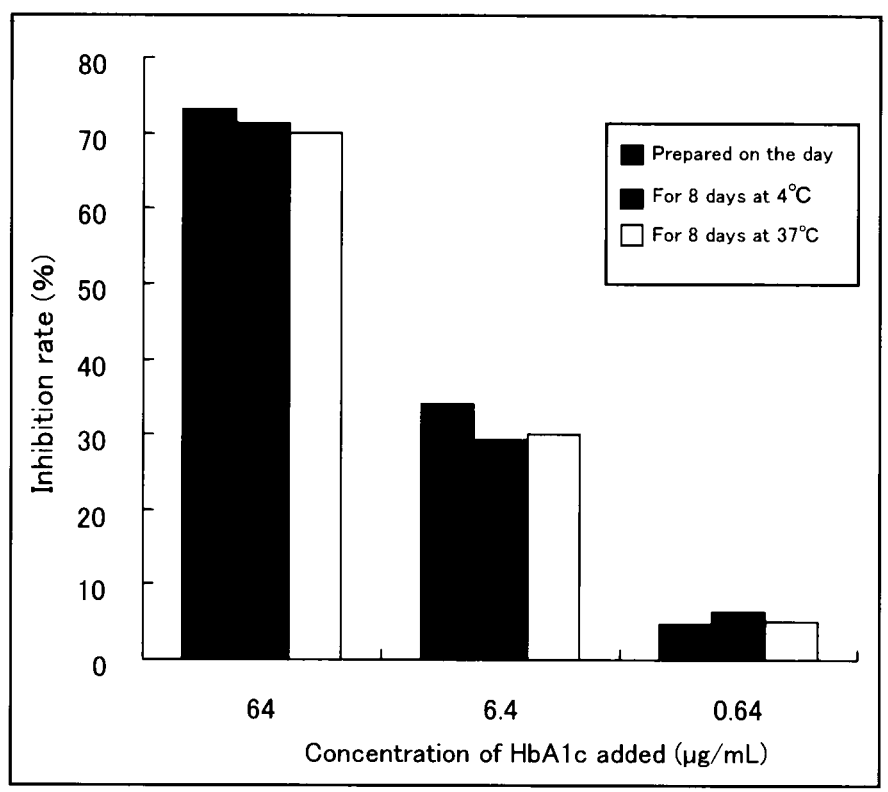
FIG. 3 shows the results of an examination of the storage stability of the reagent of the present invention, obtained by a competitive ELISA method.

As a result, as shown in FIG. 3, the effects of epitope exposure were almost equal in the reagent which was left to stand for 8 days at 37° C. and in the reagent prepared on the test day. From these results, it was found that the reagent for epitope exposure of the present invention was satisfactory in the storage stability.

Example 3

Verification of Practical Usability (I) Materials and Methods (1) Preparation of Anti-HbA1c Antibody, Anti-Hemoglobin Antibody, and Anti-HbA0 Antibody The anti-HbA1c antibody, anti-hemoglobin antibody, and anti-HbA0 antibody used in the measurement were prepared in the same manner as in the section (3) of Example 1.

(2) Preparation of Biotin-Labeled Anti-Hemoglobin Antibody

The anti-hemoglobin antibody of the above section (1) was labeled as follows, using a commercially available biotin label reagent (Pierce Biotechnology, Inc.; EZ-Link Sulfo-NHS-LC-Biotin). 0.05 mL of the biotin label reagent which had been dissolved in PBS to a concentration of 10 mg/mL, was added to 1 mL of an anti-hemoglobin antibody solution at a concentration of 1 mg/mL, and the mixture was allowed to react for 2 hours at room temperature. After the reaction, the antibody was dialyzed with PBS and then was used in the assay.

(3) Preparation of Specimen and Standard Sample

Blood was collected from employee volunteers using EDTA-2Na-containing vacuum blood collection tubes (manufactured by Sekisui Medical Co., Ltd.), and red blood cells were separated by centrifugation. 4 μl of these red blood cells were mixed with 200 μL of the pre-treatment solution of the present invention (1% polyoxyethylene sorbitan monolaurate (Tween 20)–mmol/L $NaNO_2$–3 mol/L guanidine hydrochloride–5 mmol/L MES, pH 6.0). The mixture was left to stand for 10 minutes at 25° C., and then the mixture was diluted stepwise with 3% skimmed milk-PBST. This dilution was used as a specimen for sandwich ELISA as follows. Furthermore, for a standard sample, a specimen of another person of which the HbA1c concentration and the HbA0 concentration had been previously determined by a HPLC method as described below was used.

(4) Measurement of HbA0 Concentration by Sandwich ELISA a. An anti-HbA0 antibody was diluted with PBS to a concentration of 5 μg/mL. This dilution was dispensed on an ELISA plate in an amount of 50 μL/well, and the plate was left to stand overnight at 4° C.

b. The plate was washed three times with PBST (350 μL/well), and then 1% BSA-PBST was dispensed on the plate in an amount of 100 μL/well. The plate was left to stand for one hour at room temperature.

c. The plate was washed three times with PBST, and then the standard sample or specimen which had been treated in the above section (3) was dispensed on the plate in an amount of 50 μL/well. The plate was left to stand for one hour at room temperature.

d. The plate was washed three times with PBST, and then the biotin-labeled anti-hemoglobin antibody which was diluted with 1% BSA-PBST to a concentration of 1 μg/mL was dispensed on the plate in an amount of 50 μL/well. The plate was left to stand for one hour at room temperature.

e. The plate was washed three times with PBST, and then HRP-Streptavidin (manufactured by Pierce Biotechnology, Inc.) which was diluted with 1% BSA-PBST to a concentration of 1 μg/mL was dispensed on the plate in an amount of 50 μL/well. The plate was left to stand for 30 minutes at room temperature.

f. The plate was washed three times with PBST, and then the OPD color developing solution was dispensed on the plate (50 μL/well). The plate was left to stand for 10 minutes at room temperature.

g. 0.75 mol/L sulfuric acid was dispensed on the plate in an amount of 50 μL/well to stop the reaction, and then the absorbance at 492 nm was measured with a plate reader.

h. A calibration curve was produced based on the absorbance of the standard sample at various concentrations, and the concentration of the specimen was determined using the calibration curve.

(5) Measurement of HbA1c Concentration by Sandwich ELISA

The HbA1c concentration was measured by the same method as that used in the above section (4), using an anti-HbA1c antibody instead of the anti-HbA0 antibody.

(6) Calculation of HbA1c Value

The HbA1c value (content of HbA1c) was determined by the following calculation formula, based on the HbA0 concentration and HbA1c concentration determined in the above sections (4) and (5).

<Calculation Formula>

HbA1c content (%)=(Amount (concentration) of HbA1c/(amount (concentration) of HbA1c+ amount (concentration) of HbA0))×100

(7) Measurement of HbA1c Value by HPLC Method

The proportion of HbA1c in the total amount of hemoglobin was measured using a Tosoh automatic glycohemoglobin analyzer, HLC-723 G8.

(II) Results (1) Calibration Curve

Figure 4:
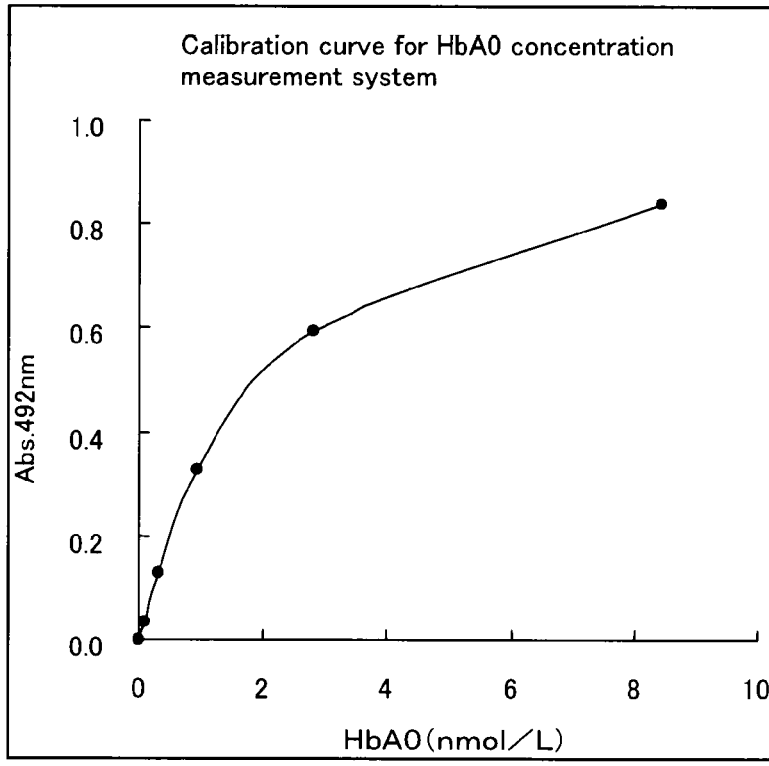
FIG. 4 shows calibration curves for a HbA1c concentration measurement system and a HbA0 concentration measurement system based on sandwich ELISA using the reagent of the present invention.
Figure 4:
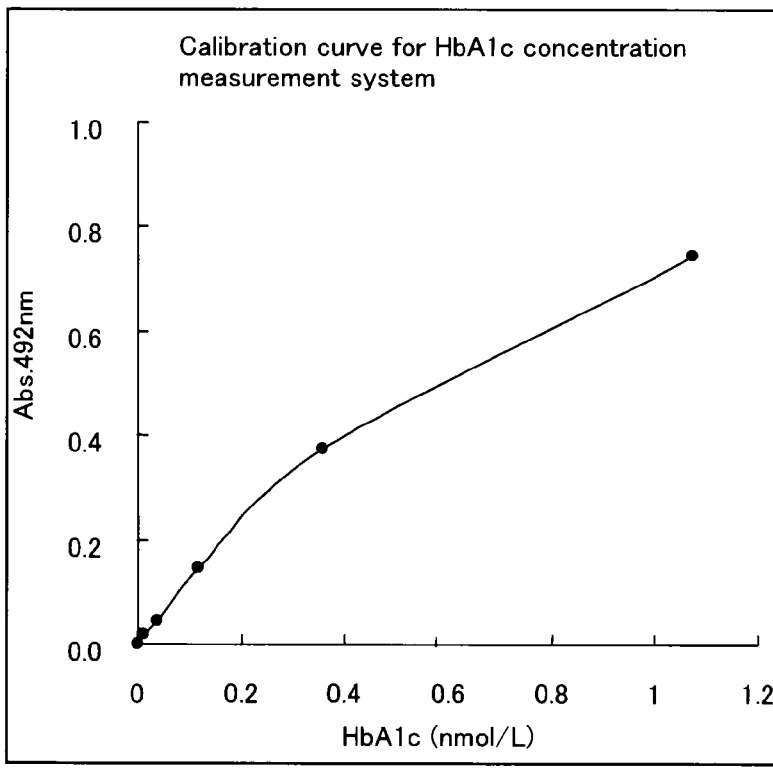

Calibration curves for a HbA0 concentration measurement system and a HbA1c concentration measurement system were produced by using standard samples. As shown in FIG. 4, an antigen concentration-dependent increase in the absorbance was confirmed in both measurement systems.

(2) Comparison with Measurement Values by HPLC Method

The HbA1c values determined by the sandwich ELISA described above using the pre-treatment solution of the present invention were compared with the HbA1c values determined by the HPLC method. The HbA1c values of specimens collected from five normal subjects were determined respectively by both methods. As a result, as shown in Table 3, the HbA1c values determined by both methods were approximately the same.

TABLE 3

| | HbA1c(%) | |
|---|---|---|
| No. | Tosoh HPLC | Sandwich ELISA |
| 1 | 5.2 | 5.3 |
| 2 | 5.2 | 4.5 |
| 3 | 4.8 | 4.4 |
| 4 | 4.8 | 5.2 |
| 5 | 5.0 | 5.5 |

From the results shown above, it was confirmed that the pre-treatment solution of the present invention can be used in a quantitative assay of the HbA0 concentration, HbA1c concentration and HbA1c value (proportion of HbA1c).

The invention claimed is:

1. A method for conducting an immunological assay comprising pre-treating a glycated hemoglobin-containing sample for said immunological assay without a heating treatment wherein said pre-treating comprises: treating a glycated hemoglobin-containing sample with a pre-treatment solution containing (A) 1 to 6 mol/L guanidine or a salt thereof and (B) 0.1 to 5% of a nonionic surfactant and nitrite in an amount ranging from 5 to 15 mmol/L, wherein said nonionic surfactant is selected from the group consisting of polyoxyethylene(23) lauryl ether, N,N-bis(3-D-gluconamidopropyl)deoxycholamide, methyl-6-O—(N-heptylcarbamoyl)-α-D glucopyranoside (HECAMEG), n-octanoyl-N-methylglucamide (MEGA-8), n-nonanoyl-N-methylglucamide (MEGA-9), n-decanoyl-N-methylglucamide (MEGA-10), n-octyl-β-glucopyranoside, polyoxyethylene(80) polyoxypropylene(30) polyoxyethylene(80) (Pluronic F-68), polyoxyethylene sorbitan monolaurate (Tween 20), polyoxyethylene sorbitan monolaurate (Tween 80), polyoxyethylene nonyl phenyl ether (Nonidet P40), sucrose monolaurate, polyoxyethylene octyl phenyl ether (Triton X-100), polyoxyethylene octyl phenyl ether (Triton X-114), n-dodecyl-β-D-maltoside (DDM), octyl-β-D-thioglucopyranoside, and saponin; and conducting said immunological assay comprising:
forming a specific antigen-antibody complex by contacting said glycated hemoglobin-containing sample following said pre-treating with an anti-glycated hemoglobin antibody, and
assaying for glycated hemoglobin by detecting presence of said specific antigen-antibody complex.

2. The method according to claim 1, wherein said non-ionic surfactant is selected from the group consisting of polyoxyethylene(23) lauryl ether, N,N-bis(3-D-gluconamidopropyl)deoxycholamide, methyl-6-O—(N-heptylcarbamoyl)-α-D-glucopyranoside (HECAMEG), n-nonanoyl-N-methylglucamide (MEGA-9), n-decanoyl-N-methylglucamide (MEGA-10), n-octyl-β-glucopyranoside, polyoxyethylene(80) polyoxypropylene(30) polyoxyethylene(80) (Pluronic F-68), polyoxyethylene sorbitan monolaurate (Tween 20), polyoxyethylene sorbitan monolaurate (Tween 80), polyoxyethylene nonyl phenyl ether (Nonidet P40), sucrose monolaurate, polyoxyethylene octyl phenyl ether (Triton X-100), polyoxyethylene octyl phenyl ether (Triton X-114), n-dodecyl-β-D-maltoside (DDM), octyl-β-D-thioglucopyranoside, and saponin and wherein said nonionic surfactant is present in said pre-treatment solution in an amount ranging from 0.25 to 1%.

3. The method according to claim 1, wherein said non-ionic surfactant is n-octanoyl-N-methylglucamide (MEGA-8) and said octanoyl-N-methylglucamide (MEGA-8) is present in said pre-treatment solution in an amount ranging from 1 to 5%.

4. The method according to claim 1, wherein said immunological assay is selected from the group consisting of a sandwich ELISA method, a competitive ELISA method, an immunochromatographic method, a latex agglutination method, and a competitive latex agglutination method.

5. The method according to claim 1, wherein said pre-treatment solution comprises guanidine or a salt thereof at a concentration ranging from 2.5 to 3.5 mol/L.

6. The method according to claim 5, wherein said non-ionic surfactant is selected from the group consisting of polyoxyethylene(23) lauryl ether, N,N-bis(3-D-gluconamidopropyl)deoxycholamide, methyl-6-O—(N-heptylcarbamoyl)-α-D-glucopyranoside (HECAMEG), n-nonanoyl-N-methylglucamide (MEGA-9), n-decanoyl-N-methylglucamide (MEGA-10), n-octyl-β-glucopyranoside, polyoxyethylene(80) polyoxypropylene(30) polyoxyethylene(80) (Pluronic F-68), polyoxyethylene sorbitan monolaurate (Tween 20), polyoxyethylene sorbitan monolaurate (Tween 80), polyoxyethylene nonyl phenyl ether (Nonidet P40), sucrose monolaurate, polyoxyethylene octyl phenyl ether (Triton X-100), polyoxyethylene octyl phenyl ether (Triton X-114), n-dodecyl-β-D-maltoside (DDM), octyl-β-D-thioglucopyranoside, and saponin and wherein said nonionic surfactant is present in said pre-treatment solution in an amount ranging from 0.25 to 1%.

7. The method according to claim 5, wherein said non-ionic surfactant is n-octanoyl-N-methylglucamide (MEGA-8) and said octanoyl-N-methylglucamide (MEGA-8) is present in said pre-treatment en solution in an amount ranging from 1 to 5%.

8. A method for measuring content of glycated hemoglobin in a glycated hemoglobin-containing sample, comprising:
   treating said glycated hemoglobin-containing sample with a pre-treatment solution containing (A) 1 to 6 mol/L guanidine or a salt thereof and (B) 0.1 to 5% of a non-ionic surfactant and nitrite in an amount ranging from 5 to 15 mmol/L to provide a treated sample, and
   conducting an immunological assay comprising
      forming a specific antigen-antibody complex by contacting said glycated hemoglobin-containing sample following said treating with an anti-glycated hemoglobin antibody, and
      detecting presence and amount of said specific antigen-antibody complex as indicative of the content of glycated hemoglobin in said glycated hemoglobin-containing sample,
   wherein said nonionic surfactant is selected from the group consisting of polyoxyethylene(23) lauryl ether, N,N-bis(3-D-gluconamidopropyl)deoxycholamide, methyl-6-O—(N-heptylcarbamoyl)-α-D-glucopyranoside (HECAMEG), n-octanoyl-N-methylglucamide (MEGA-8), n-nonanoyl-N-methylglucamide (MEGA-9), n-decanoyl-N-methylglucamide (MEGA-10), n-octyl-β-glucopyranoside, polyoxyethylene(80) polyoxypropylene(30) polyoxyethylene(80) (Pluronic F-68), polyoxyethylene sorbitan monolaurate (Tween 20), polyoxyethylene sorbitan monolaurate (Tween 80), polyoxyethylene nonyl phenyl ether (Nonidet P40), sucrose monolaurate, polyoxyethylene octyl phenyl ether (Triton X-100), polyoxyethylene octyl phenyl ether (Triton X-114), n-dodecyl-β-D-maltoside (DDM), octyl-β-D-thioglucopyranoside, and saponin, and
   wherein said treating with a pre-treatment solution is conducted without a heating treatment and said immunological assay is selected from the group consisting of a sandwich enzyme-linked immunosorbent assay (ELISA) method, a competitive ELISA method, an immunochromatographic method, a latex agglutination method, and a competitive latex agglutination method.

9. The method according to claim 8, wherein said non-ionic surfactant is selected from the group consisting of polyoxyethylene(23) lauryl ether, N,N-bis(3-D-gluconamidopropyl)deoxycholamide, methyl-6-O—(N-heptylcarbamoyl)-α-D-glucopyranoside (HECAMEG), n-nonanoyl-N-methylglucamide (MEGA-9), n-decanoyl-N-methylglucamide (MEGA-10), n-octyl-β-glucopyranoside, polyoxyethylene(80) polyoxypropylene(30) polyoxyethylene(80) (Pluronic F-68), polyoxyethylene sorbitan monolaurate (Tween 20), polyoxyethylene sorbitan monolaurate (Tween 80), polyoxyethylene nonyl phenyl ether (Nonidet P40), sucrose monolaurate, polyoxyethylene octyl phenyl ether (Triton X-100), polyoxyethylene octyl phenyl ether (Triton X-114), n-dodecyl-β-D-maltoside (DDM), octyl-β-D-thioglucopyranoside, and saponin and wherein said nonionic surfactant is present in said pre-treatment solution in an amount ranging from 0.25 to 1%.

10. The method according to claim 8, wherein said non-ionic surfactant is n-octanoyl-N-methylglucamide (MEGA-8) and said octanoyl-N-methylglucamide (MEGA-8) is present in said pre-treatment solution in an amount ranging from 1 to 5%.

11. The method according to claim 8, wherein said pre-treatment solution comprises guanidine or a salt thereof at a concentration ranging from 2.5 to 3.5 mol/L.

12. The method according to claim 11, wherein said non-ionic surfactant is selected from the group consisting of polyoxyethylene(23) lauryl ether, N,N-bis(3-D-gluconamidopropyl)deoxycholamide, methyl-6-O—(N-heptylcarbamoyl)-α-D-glucopyranoside (HECAMEG), n-nonanoyl-N-methylglucamide (MEGA-9), n-decanoyl-N-methylglucamide (MEGA-10), n-octyl-β-glucopyranoside, polyoxyethylene(80) polyoxypropylene(30) polyoxyethylene(80) (Pluronic F-68), polyoxyethylene sorbitan monolaurate (Tween 20), polyoxyethylene sorbitan monolaurate (Tween 80), polyoxyethylene nonyl phenyl ether (Nonidet P40), sucrose monolaurate, polyoxyethylene octyl phenyl ether (Triton X-100), polyoxyethylene octyl phenyl ether (Triton X-114), n-dodecyl-β-D-maltoside (DDM), octyl-β-D-thioglucopyranoside, and saponin and wherein said nonionic surfactant is present in said pre-treatment solution in an amount ranging from 0.25 to 1%.

13. The method according to claim 11, wherein said non-ionic surfactant is n-octanoyl-N-methylglucamide (MEGA-8) and said octanoyl-N-methylglucamide (MEGA-8) is present is said pre-treatment solution in an amount ranging from 1 to 5%.

* * * * *